United States Patent
Patel et al.

(10) Patent No.: US 6,526,304 B1
(45) Date of Patent: Feb. 25, 2003

(54) METHOD AND APPARATUS FOR PROCESSING PICTURE ARCHIVING AND COMMUNICATIONS SYSTEM IMAGES

(75) Inventors: Maqbol Patel, Bangalore (IN); David McKone, Ann Arbor, MI (US)

(73) Assignee: General Electric Company, Schnectady, NY (US)

( * ) Notice: Subject to any disclaimer, the term of this patent is extended or adjusted under 35 U.S.C. 154(b) by 0 days.

(21) Appl. No.: 09/473,521

(22) Filed: Dec. 28, 1999

(51) Int. Cl.[7] .................................................. A61B 5/05
(52) U.S. Cl. ........................ 600/407; 128/920; 128/922; 382/128; 382/162
(58) Field of Search ................................ 382/128, 130, 382/131, 162; 600/407, 410, 437, 425, 436, 473, 476; 430/398; 128/920, 922, 897, 898

(56) References Cited

U.S. PATENT DOCUMENTS

| | | | |
|---|---|---|---|
| 4,652,999 A | | 3/1987 | Higashi et al. |
| 4,843,471 A | * | 6/1989 | Yazawa et al. ............. 358/160 |
| 5,150,421 A | * | 9/1992 | Morishita et al. ........... 382/128 |
| 5,542,003 A | * | 7/1996 | Wofford ...................... 345/660 |
| 5,600,574 A | * | 2/1997 | Reitan ......................... 364/552 |
| 5,740,267 A | * | 4/1998 | Echerer et al. ............. 382/132 |
| 5,884,005 A | * | 3/1999 | Peters ......................... 386/109 |
| 5,920,317 A | * | 7/1999 | McDonald .................. 345/835 |
| 6,269,176 B1 | * | 7/2001 | Barski et al. ............... 128/922 |
| 6,289,115 B1 | * | 9/2001 | Takeo ......................... 128/920 |
| 6,363,163 B1 | * | 3/2002 | Xu et al. ..................... 382/130 |

OTHER PUBLICATIONS

Fuji CR Processing web pages (22 pages), author unknown, date unknown, <http://www.funjindt.com/medical>, printed Nov. 18, 1999.
"PACS Basic Principles and Applications", H.K. Huang, D.Sc., Chapters 7,8,12, pps. 199–231, 305–342, 177–198.

\* cited by examiner

*Primary Examiner*—Marvin M. Lateef
*Assistant Examiner*—Jeoyuh Lin
(74) *Attorney, Agent, or Firm*—McAndrews, Held & Malloy, Ltd.; Peter J. Vogel; Michael A. Dellapenna

(57) ABSTRACT

A method for processing images in a Picture Archiving and Communications System (PACS) is provided. The method includes imaging a patient with an imaging modality to generate raw digital image data and then sending the raw image data to an acquisition workstation. The acquisition workstation then partially processes the raw image data with regard to a predetermined subset of the set of control parameters to form a partially processed image. The subset of control parameters may comprise frequency control parameters or contrast control parameters, for example. The partially processed image may then be sent to an external connection, stored in a database in the PACS, or sent to a display workstation for complete processing and display. A partially processed image that has been stored in a database in the PACS may be retrieved and sent to a display workstation for complete processing and display. The completely processed image may be sent to an external connection, for example, for transmission through an external network, such as the internet.

27 Claims, 3 Drawing Sheets

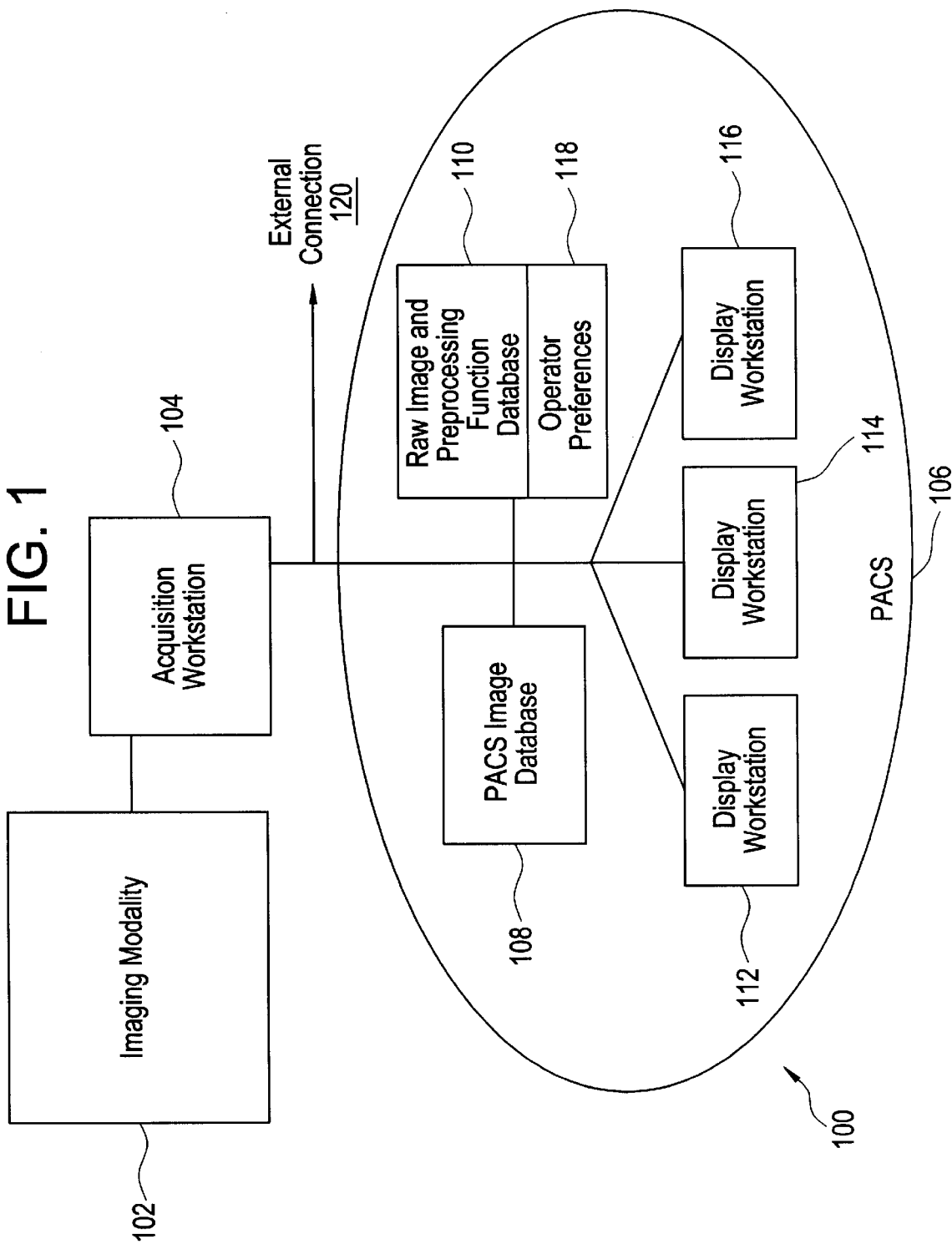

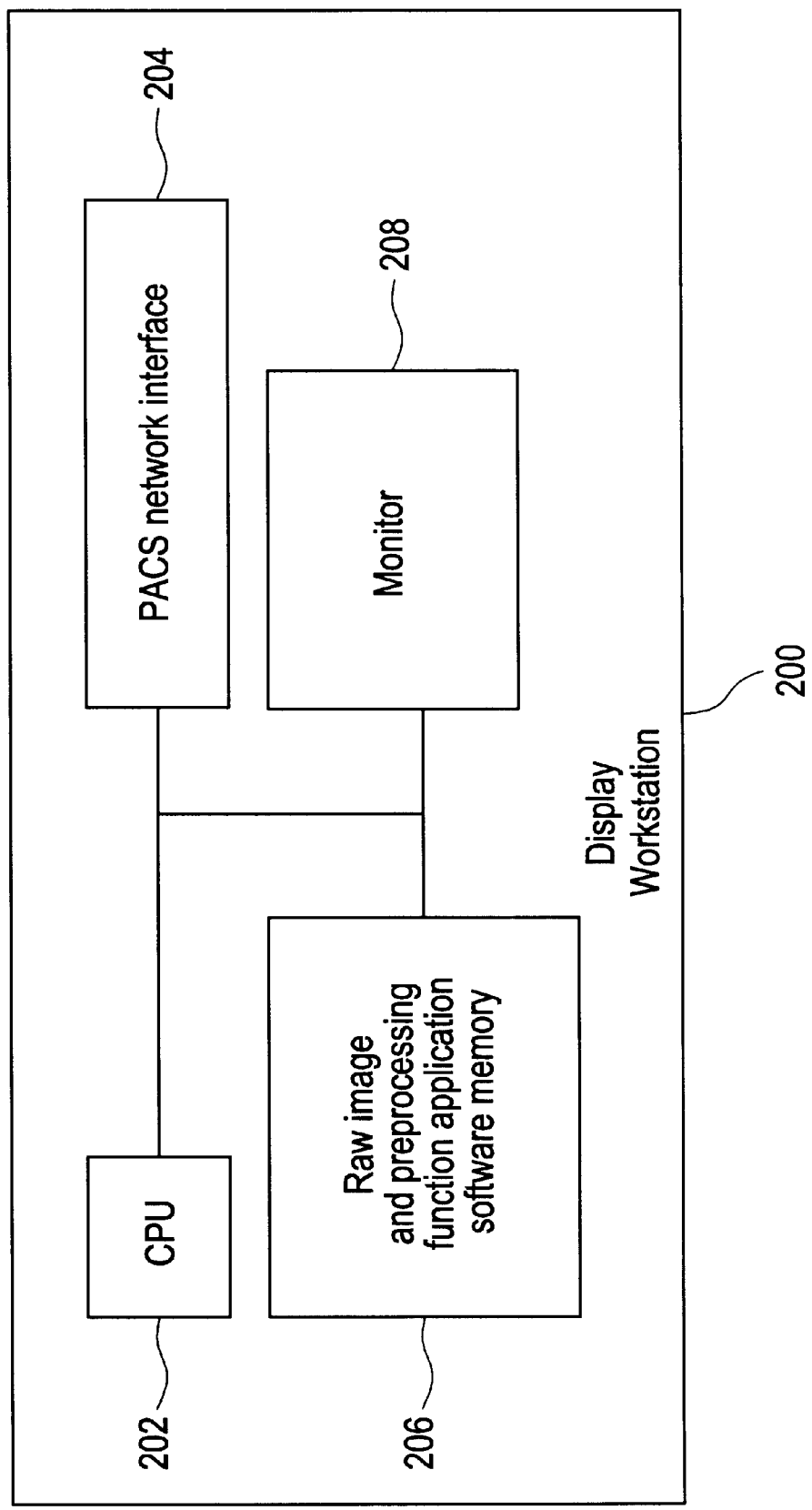

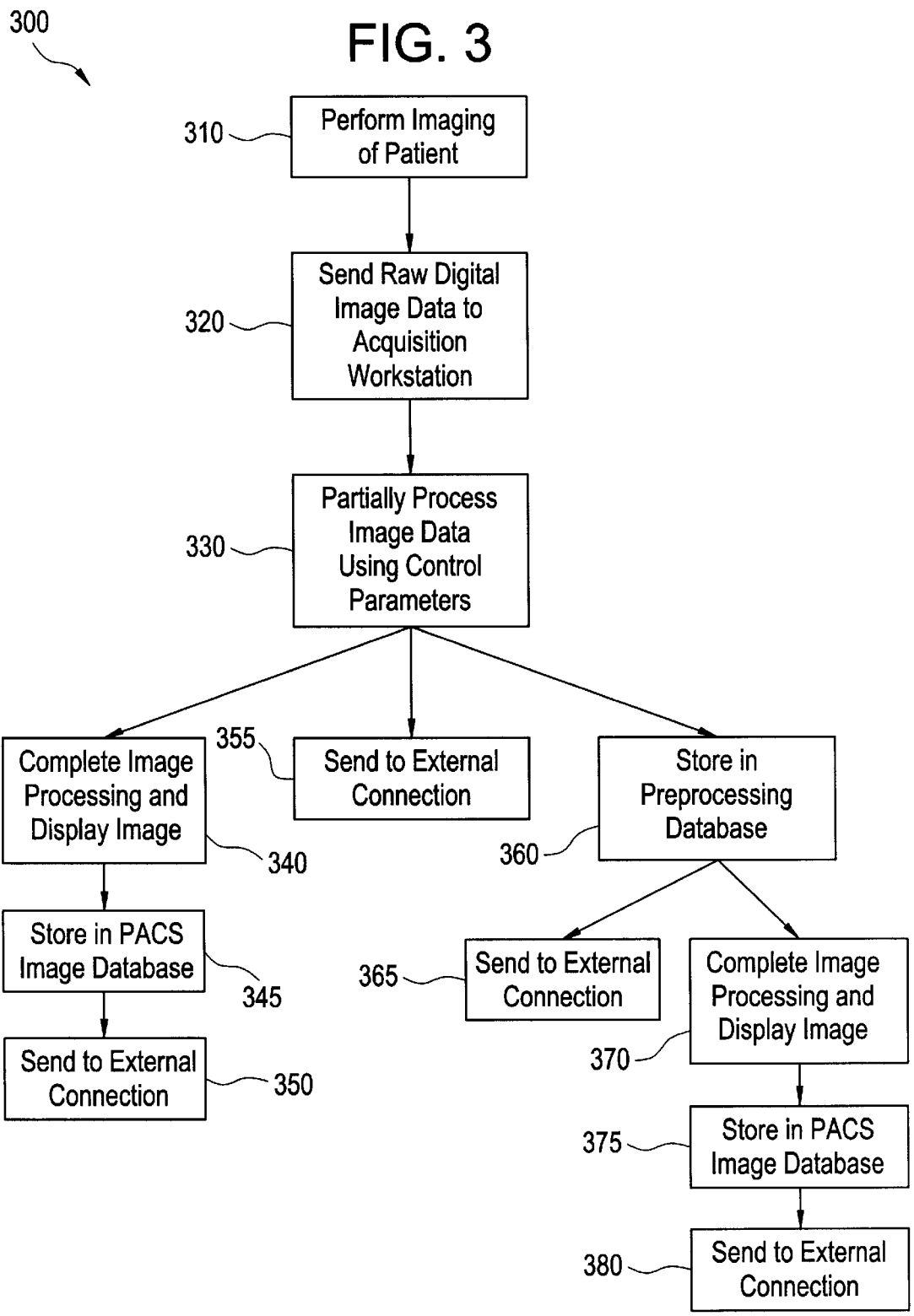

METHOD AND APPARATUS FOR PROCESSING PICTURE ARCHIVING AND COMMUNICATIONS SYSTEM IMAGES

BACKGROUND OF THE INVENTION

The present invention generally relates to improvements in a Picture Archiving and Communications System (PACS), and more particularly relates to a method for improved processing of PACS images and a system for implementing such.

A PACS is one of the latest generation of devices for medical diagnosis, storage, communication, and visualization. Typically, a PACS is implemented in conjunction with the medical imaging capabilities of hospital diagnostic equipment such as an X-ray imaging, ultrasound imaging, Magnetic Resonance Imaging (MRI), CAT scan, or other imaging device. The type of diagnostic imaging equipment is typically generically referred to as the imaging modality. Using an ultrasound system as an example, prior art ultrasound systems have typically been incarnated as stand-alone devices. Such stand-alone systems typically possess a display screen for observation of the ultrasonic diagnosis or are able to generate a printed image of a snapshot of the diagnosis. Such stand-alone systems typically were not able to electronically store images due to real-time processing constraints and storage capacity constraints.

However, recent improvements in the computing and networking fields have lead to the development of PACS systems, that is, systems that are able to store or archive the massive quantities of digital information that comprise each digital diagnostic image. Networking advancements have lead to the development of networks of sufficient bandwidth to transport such massive digital diagnostic images away from the stand-alone imaging device to a dedicated computer network, typically within the same facility. Once the data underlying the diagnostic image has been communicated to the dedicated network, the image may be stored, processed, re-analyzed, reproduced, or re-transmitted, for example. A PACS thus provides a large increase in flexibility of image treatment. An image of the patient may be stored and analyzed in several fashions, or may be transmitted to a specialist for review, for example.

However, because of the demands of processing huge-bandwidth images such as diagnostic images, present PACS systems operate in one of two ways. The first manner of operation positions a high-end workstation, such as an AMBER workstation as a gateway between the modality and the PACS. The workstation processes the digital data representing the diagnostic image received from the modality, typically in real time. The final processed image is then relayed to a storage medium within the PACS for later use. Typically, the processing employed by the workstation is in response to user-configured parameters such as frequency, contrast, or depth of the image. Typically, the workstation receives the raw digital data from the modality, processes the raw data to optimize the user-configured parameters, and then stores the final, processed image.

Also, typically, the massive amounts of digital data received by the workstation, once combined into a final image, are greatly reduced in size. However, once the final image has been supplied to the storage medium, very little further processing may be applied to the image. The amount of further processing is limited because the processing of the workstation typically eliminates data that is extraneous to the user-configured parameters. That is, for example, if an ultrasonic image at a depth of two inches within the patient is desired, the modality may still receive the entirety of the ultrasonic signal corresponding to a variable depth within the patient. The workstation typically receives the raw digital signal, synthesizes the desired image, and relays the image to the storage medium. If an image at a different depth is desired, a new diagnostic image must be performed. Because the workstation's processing constraints dictate a high-end workstation, the first type of PACS systems are typically equipment-expensive. However, because the output of the workstation is typically a smaller image file, the first type of PACS systems are typically bandwidth-efficient. Bandwidth efficiency may often be preferable because it may allow the sharing or communication of the resultant digital images over commercial, non-dedicated networks such as the internet. However, the transmitted image may not be further manipulated.

The second type of PACS typically eliminates the workstation, or substitutes a reduced-application workstation that provides little processing, if any. In the second type of PACS system, the raw digital data is transported directly to a storage medium within the PACS without substantial processing. The raw digital data may then be retrieved from the storage medium for later non-real-time processing on a mid- to lower-end workstation that would be unable to process the raw digital information in real time. Although the second type of PACS may be less equipment-expensive with the elimination of the high-end workstation, the addition of the high-bandwidth communication channel directly to the PACS and the addition of a very fast storage medium represent significant cost. Also, the intra-networking of the PACS itself must be supplemented to reflect the vastly larger raw digital files that must be transported. In addition, the large, raw digital files are typically not externally transportable via less expensive non-dedicated communications channels, such as the internet, because of their size. Although the second type of PACS may be employed to generate processed digital images similar to the processed digital images supplied by the high-end workstation of the first type of PACS, because of the lesser scale of the workstation of the second type of PACS, the repeated formulation of such images may be quite time consuming. The formation of such images may become especially time-consuming if the PACS system is in use by more than one clinician or at more than one site, as is typically the case. The internal bandwidth constraints of the second type of PACS system may be especially severe if new raw data is being received from a modality at the same time as previously received data is being supplied to the workstation. Thus, although the second-type of PACS may provide a lower cost option, networking and bandwidth difficulties may make the second type of PACS inapplicable in a large clinical setting. In addition, while the raw digital data may reside in storage in the second type of PACS, and may thus be available to form images corresponding to differing user parameters, in a multi-user environment use of the second type of PACS system to perform multi-image analysis may not be practical.

As will be appreciated, the two types of PACS are not interchangeable without large-scale infrastructure expenditures. That is, to switch from one type of system to the other, either a high-end workstation must be procured or a high-bandwidth network must be installed.

Thus, a need has long existed for an improved PACS system providing improved imaging flexibility at a less expensive equipment and networking cost. A need has also long existed for a cost and practically effective system for allowing clinicians to perform multi-image analysis. Additionally, a need has long existed for a cost-effective system for transporting manipulatable image files through a commercial, non-dedicated network such as the internet.

BRIEF SUMMARY OF THE INVENTION

The preferred embodiments of the present invention provide a method and apparatus for processing images in a Picture Archiving and Communications Systems (PACS). The preferred embodiments of the present invention maximize computational efficiency, cost efficiency, network bandwidth efficiency and image manipulation flexibility. The preferred embodiments perform partial preprocessing of raw digital image data received from a modality at an acquisition workstation and then store the partially processed image data on the PACS. Preferably, the preprocessing at the acquisition workstation is performed on frequency-control related parameters while contrast-related parameters remain unprocessed, although contrast control parameters may also be used. The partially processed image data may be retrieved later from the PACS and the processing completed with user-selected and variable parameters at an image workstation. Fully processed images may then be stored in a PACS image data base. In addition partially or fully processed images may be transmitted to an external network such as the internet.

BRIEF DESCRIPTION OF THE DRAWINGS

FIG. 1 presents a high level block diagram of a diagnostic data network including a PACS system in accordance with a preferred embodiment of the present invention.

FIG. 2 illustrates a PACS display workstation suitable for use in the PACS system of FIG. 1.

FIG. 3 illustrates a flow chart of a method for processing images in accordance with a preferred embodiment of the present invention.

DETAILED DESCRIPTION OF THE INVENTION

FIG. 1 illustrates an improved medical diagnostic data system 100 according to a preferred embodiment of the present invention. The system 100 includes an imaging modality 102, an acquisition workstation 104, external network connection 120, and an improved PACS network 106. The PACS network 106 includes a PACS image database 108, a raw image data and preprocessing function database 110 ("preprocessing database 110"), and display workstations 112, 114, 116. A set of operator preferences 118 is stored in the preprocessing database 110.

As mentioned above, he imaging modality 102 is typically a medical diagnostic imaging device of some sort. For example, the imaging modality 102 may perform X-ray imaging, ultrasound imaging, Magnetic Resonance Imaging (MRI), CAT scan imaging, or other imaging. The imaging modality 102 is connected to the acquisition workstation 104 using, for example, a high-bandwidth network connection or dedicated interface port. During operation, the imaging modality 102 generates raw digital image data corresponding to the particular modality of the imaging modality 102, for example raw digital x-ray data.

The acquisition workstation 104 accepts raw digital image data from the imaging modality 102. The acquisition workstation 104 may then perform preprocessing or partial processing on the raw image data (as described in more detail below). The partially processed image data is then delivered to the PACS network 106 for storage in the PACS image database 108 or preprocessing database 110, for example. The acquisition workstation 104 may also partially process raw image data to reformat modality-specific imaging data into a more generic data form such as DICOM. The components of the PACS network 106 have been chosen to provide an example. In practice, the PACS network 106 may include many other components such as additional storage, additional workstations, imaging devices such as printers, graphic rendering stations, etc.

The PACS image database 108 and the preprocessing database 110 are illustrated in FIG. 1 for convenience as separate databases. However, they may be a single database, separate databases on an single computer, or separate databases distributed among different computers. In general, the PACS image database 108 stores fully preprocessed images (i.e., those images for which no additional preprocessing or partial processing functions will be applied). On the other hand, the preprocessing database 110 stores partially preprocessed image data ("raw digital image data") (i.e., that image data that has not yet been completely preprocessed).

The display workstations 112–116 are coupled to the PACS image database 108 and the preprocessing database 110. Thus, the display workstations 112–116 may retrieve images from the PACS image database 108 for immediate modification and display or the display workstations 112–116 may retrieve partially processed image data from the preprocessing database 110. When the display workstations 112–116 retrieve partially processed image data, however, the raw image data is further modified by preprocessing functions to form resultant image data. The resultant image data may then represent a fully preprocessed image, or may require additional preprocessing before being stored as a fully preprocessed image.

The external network connection 120 may be used to connect the PACS system 106 with an external network such as the internet. Alternatively, the external connection 120 may connect to a disc drive, CD-ROM drive or other data writing device that may allow data from the PACS system 106 to be transported.

As mentioned above, the acquisition workstation 104 performs partial processing on the raw digital image data received from the image modality 102. In general, each image modality 102 has several image parameters associated with the raw digital image data that it provides to the acquisition workstation 104. The image parameters may vary between modalities and between manufacturers. For example, an x-ray system manufactured by Fuji may not share identical image parameters with a x-ray system from a different x-ray manufacturer, or even with an ultrasound system manufactured by Fuji. However, in general, the image parameters associated with each modality may be grouped into known parameter classes, such as for example frequency control parameters or contrast control parameters. Clinically, frequency control parameters are rarely adjusted, possibly because resolution of a diagnostic image may increase with frequency and usually maximal diagnostic resolution is desired. Conversely, contrast control parameters may often be adjusted during the course of a clinical session in order to increase the sharpness, depth, or brightness of an image.

Using an CR system from Fuji as an example, the Fuji system frequency control parameters may include: RN (Frequency Rank), RE (Frequency Enhancement), and RT (Frequency Type). The Fuji system contrast control parameters may include: GT (Contrast Type), GA (Rotation amount of the basic contrast (GT) curve), GC (Rotation center for the GT curve), GS (Density shift, amount of shifting applied to GT). Thus, the raw digital image data received from the imaging modality 102 by the acquisition workstation 104 is partially processed with regard to the frequency control parameters RN, RE, and RT. The partially processed image may then be stored on the preprocessing database 110. The partially processed image may be either immediately further processed at a display workstation 112–116 if an immediate image display is desired. Alternatively, the partially processed image may be later retrieved and manipulated on a display workstation 112–116.

The stored partially processed image may be retrieved and extensively manipulated. The image has only been processed with regard to its frequency control parameters. Contrast control parameters (and consequently the dynamic range of the image) remain in their raw digital image data form, and no information has been eliminated with regard to these parameters. A clinician may retrieve such a partially processes image at any of the display workstations 112–116 and manipulate it at any time.

Although the acquisition workstation 104 must process the raw image data it receives from the imaging modality 102 in real time, because the acquisition workstation 104 only performs partial processing relating to the frequency control parameters rather than processing the entire parameter set, the acquisition workstation 104 need not have the processing power of a high-end workstation as discussed in the background section above with regard to the first type of PACS system. Because of the lesser demand for processing power, the acquisition workstation 104 may by composed of a less expensive workstation such as a low end SPARC Station workstation available from SUN Microsystems.

Alternatively, the acquisition workstation 104 may be reconfigured by a clinician to perform partial processing on the contrast control parameters rather than frequency control parameters. However, processing the contrast control parameters in many instances may yield a considerably less manipulatable and consequently less diagnostically useful image.

FIG. 2 illustrates a PACS display workstation 200 such as display workstations 112–116 suitable for use in the PACS network 106. The display workstation 200 includes a general purpose central processing unit (CPU) 202, a PACS network interface 204, a software memory 206, and an image display monitor 208. The PACS network interface 204 is typically implemented as a network card connecting to a TCP/IP based network, but may also be implemented as a parallel port interface, or the like. In particular, the software memory 206 is a raw image and preprocessing function software memory.

Thus, the software memory 206 includes, for execution by the processing circuit 202, instructions for retrieving, from a PACS database, raw image data delivered from an imaging modality. The instructions also allow the operator at the PACS workstation 200 to select a preprocessing function for the raw image data. Once the raw image data and the preprocessing function are determined, the instructions in the software memory 206 allow the processing circuit 202 to apply the preprocessing function to the raw image data to create resultant image data. For example, the software memory 206 may perform further processing, such as contrast control parameter processing, on frequency preprocessed raw image data that has been retrieved from the preprocessing database 110 of FIG. 1.

FIG. 3 illustrates a flowchart 300 of a preferred embodiment of the present invention. First, at step 310, imaging is performed on the patient according to the present modality. Next, at step 320, the raw digital image data is sent from the imaging modality to the acquisition workstation. Then, at step 330, the acquisition workstation partially processes the image data using control parameters. Once the image data has been partially processed, the image data may be either 1) sent to a display workstation to complete the image processing and display the image at step 340, 2) sent to an external connection at step 355, or 3) stored in the preprocessing database at step 360. If the image processing was completed at step 340, the fully processed image may then be stored in the PACS image database 345. The fully processed image may also be optionally sent to the external connection for transmission to a remote network. If the image data was stored in the preprocessing database at step 360, the partially processed image data may be later optionally sent to an external connection at step 365 or the image data may be sent to a workstation to complete the image processing and display the image at step 370. The fully processed image may then be stored in the PACS image database at step 375 and may optionally be sent to an external connection for transmission to a remote network.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for processing images in a PACS comprising the steps of:
    imaging a patient with an imaging modality to form raw digital image data;
    sending the raw digital image data to an acquisition workstation; and
    partially processing said raw image data at the acquisition workstation with regard to predetermined control parameters to form a partially processed image.

2. The method of claim 1 wherein said predetermined control parameters comprises frequency control parameters.

3. The method of claim 1 wherein said predetermined control parameters comprises contrast control parameters.

4. The method of claim 1 further including the step of sending said partially processed image to an external connection.

5. The method of claim 1 further including the step of completing the image processing and displaying the image at a display workstation.

6. The method of claim 5 further including the step of storing the completely processed image in a PACS database.

7. The method of claim 6 further including the step of sending said completely processed image to an external connection.

8. The method of claim 1 further including the step of storing said partially processed image in a preprocessing database.

9. The method of claim 8 further including the step of sending said partially processed image to an external connection.

10. The method of claim 8 further including the step of completing image processing and displaying the image at a display workstation.

11. The method of claim 10 further including the step of storing the completely processed image in a PACS database.

12. The method of claim 11 further including the step of sending said completely processed image to an external connection.

13. A method for providing PACS image files for subsequent manipulation comprising the steps of:
preprocessing raw image data received from a modality with regard to predetermined control parameters to form a preprocessed image file;
storing said preprocessed image file on a preprocessing database;
retrieving said preprocessed image file from said preprocessing database;
completing the processing of said preprocessed image file to form a final processed image; and
displaying said final processed image.

14. The method of claim 13 wherein said predetermined control parameters comprises frequency control parameters.

15. The method of claim 13 wherein said predetermined control parameters comprises contrast control parameters.

16. The method of claim 13 further including the step of sending said partially processed image to an external connection.

17. The method of claim 13 further including the step of sending said final processed image to an external connection.

18. The method of claim 13 further including the step of storing the final processed image in a PACS database.

19. An improved PACS system including:
an imaging modality;
an acquisition workstation receiving raw image data from said imaging modality and partially processing said raw image data with regard to predetermined control parameters to form a partially processed image file;
a database for storing said partially processed image file; and
a display workstation for completing the processing of said preprocessed image file to form a completely processed image and displaying said completely processed image.

20. The improved PACS system of claim 19 wherein said predetermined subset of control parameters comprises frequency control parameters.

21. The improved PACS system of claim 19 wherein said predetermined subset of control parameters comprises contrast control parameters.

22. The improved PACS system of claim 19 further including an external connection for transmitting data from the PACS.

23. The improved PACS system of claim 22 wherein said partially processed image file is externally transmitted through said external connection.

24. The improved PACS system of claim 22 wherein said completely processed image file is externally transmitted through said external connection.

25. A method for forming a partially processed image for use in a PACS system, the method comprising:
receiving raw digital image data at an acquisition workstation; and
preprocessing said raw image data at the acquisition workstation with regard to predetermined control parameters to form a partially processed image.

26. The method of claim 25, further including processing said partially processed image to form a completely processed image.

27. The method of claim 26, further including:
storing said partially processed image in a preprocessing database; and
storing said completely processed image in a PACS database.

* * * * *